United States Patent [19]

Lafon

[11] Patent Number: 4,933,442

[45] Date of Patent: Jun. 12, 1990

[54] 1-(ACETYLAMINOPHENYL)-2-AMINO-PROPANONE DERIVATIVES AND CENTRAL NERVOUS SYSTEM ANTIDEPRESSANT COMPOSITIONS

[75] Inventor: Louis Lafon, Paris, France

[73] Assignee: Laboratoire L. Lafon, Maisons Alfort, France

[21] Appl. No.: 375,987

[22] Filed: Jul. 6, 1989

Related U.S. Application Data

[60] Division of Ser. No. 38,981, Apr. 16, 1987, Pat. No. 4,877,812, which is a continuation-in-part of Ser. No. 660,285, Oct. 12, 1984, abandoned.

[30] Foreign Application Priority Data

Oct. 14, 1983 [FR] France ............... 83 16408
Aug. 20, 1984 [FR] France ............... 84 12963

[51] Int. Cl.$^5$ ............ A61K 31/535; A61K 31/54; C07D 265/30; C07D 279/12
[52] U.S. Cl. ................ 514/212; 514/227.5; 514/255; 514/428; 514/238.8; 540/610; 544/58.1; 544/165; 544/399; 548/571
[58] Field of Search ............ 540/610; 544/58.1, 165, 544/399; 548/571; 514/212, 227.5, 239.8, 255, 428

[56] References Cited

U.S. PATENT DOCUMENTS

| | | | |
|---|---|---|---|
| 2,393,820 | 1/1940 | Schnider | 564/220 |
| 3,729,475 | 4/1973 | Williamson et al. | 564/219 |
| 4,138,581 | 2/1979 | Minataya et al. | 560/109 |
| 4,545,996 | 10/1985 | Lafon | 514/629 |

Primary Examiner—Richard L. Raymond
Attorney, Agent, or Firm—Wegner & Bretschneider

[57] ABSTRACT

The present invention relates, by way of new industrial products, to 1-(acetylaminophenyl)-2-amino-propanone derivatives selected from the group consisting of (a) the compounds of the formula $$Ar-CO-CH(CH_3)-NR_1R_2 \quad (I)$$

in which $R_1$ represents a $C_1$-$C_4$ alkyl group or a $C_3$-$C_6$ cycloalkyl group;

$R_2$ represents the hydrogen atom or a $C_1$-$C_4$ alkyl group;

$R_1$ and $R_2$, taken together, can form, with the nitrogen atom to which they are bonded, an N-heterocyclic group with 5 to 7 ring members, capable (i) of including a second heteroatom selected from N, O and S, and (ii) of being substituted, the said heterocyclic group $NR_1R_2$ being selected from the group comprising pyrrolidino, morpholino, thiomorpholino, piperidino, hexamethyleneimino, piperazino, 4-methylpiperazino, 4-($\beta$-hydroxyethyl) piperazino, 4-phenylpiperazino and 4-(p-chlorophenyl)-piperazino groups; and Ar represents an acetylaminophenyl group of the formula

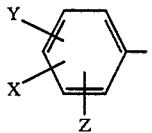

in which X is $CH_3CONH$ and Y and Z, which can be identical or different, each represent a hydrogen or halogen atom; and (b) their addition salts.

These new products are useful in therapy.

The invention also relates to the method for their preparation.

9 Claims, No Drawings

1-(ACETYLAMINOPHENYL)-2-AMINOPROPANONE DERIVATIVES AND CENTRAL NERVOUS SYSTEM ANTIDEPRESSANT COMPOSITIONS

This application is a divisional of U.S. Ser. No. 038,981 filed Apr. 16, 1987, now U.S. Pat. No. 4,877,812, which is a continuation-in-part application of U.S. Ser. No. 660,285 filed Oct. 12, 1984, now abandoned.

FIELD OF THE INVENTION

The present invention relates to new 1-(acetyl-aminophenyl)-2-aminopropanone derivatives. It also relates firstly to the use of these new derivatives in therapy, especially as antidepressants for the central nervous system (CNS), and secondly to the method for their preparation.

PRIOR ART

U.S. Pat. No. 3,644,520 (HARTLEY et al.) discloses the use of 1-(3-acetylaminomethyl-4-hydroxyphenyl)-2-aminopropanones as intermediate compounds in the synthesis of 1-(3-acetylaminomethyl-4-hydroxyphenyl)-2-aminopropanol compounds.

U.S. Pat. No. 2,393,820 (SCHNIDER) discloses the use of 1-(3-acetylamino-4-hydroxyphenyl)-2-(N-methylamino)-ethanones as intermediate compounds in the synthesis of corresponding 1-(3-acetylamino-4-hydroxyphenyl)-2-(N-methylamino)ethanol products.

U.S. Pat. No. 3,488,737 (GORDON) relates to antibacterial aminoacid derivatives wherein the terminal N atom of the aminoacid moiety is substituted by a ($CH_3CONHC_6H_5$) $COCH_2CH_2$ radical.

Some N-(acetylaminophenyl-alkylene)amines were provided or suggested as sympathomimetic and CNS-stimulant agents—see U.S. Pat. No. 4,015,011 (SCHROMM et al.)—or an anorexic, anti-hallucinogenic, anti-Parkinson and anti-inflammatory agents—see U.S. Pat. No. 3,729,475 (WILLIAMSON et al.)-.

OBJECT OF THE INVENTION

This invention is concerned with new 1-(acetylaminophenyl)-2-aminopropanone derivatives which are structurally different from the prior art compound and are useful as pharmaceuticals. These new derivatives all act of the CNS, in particular as antidepressants. In addition to the antidepressant properties common to this group of derivatives, it is found that these derivatives have stimulant (or excitant) effects on the CNS. Furthermore, some of these derivatives possess beneficial immunological and/or cardiovascular effects as indicated below.

DETAILED DISCLOSURE OF THE INVENTION

The new 1-(acetylaminophenyl)-2-aminopropanone derivatives recommended here are selected from the group consisting of (a) the compounds of the formula

   (I)

in which $R_1$ represents a $C_1$-$C_4$ alkyl group or a $C_3$-$C_6$ cycloalkyl group;

$R_2$ represents the hydrogen atom or a $C_1$-$C_4$ alkyl group;

$R_1$ and $R_2$, taken together, can form, with the nitrogen atom to which they are bonded, an N-heterocyclic group with 5 to 7 ring members, capable (i) of including a second heteroatom selected from the group comprising N, O and S, and (ii) of being substituted, the said heterocyclic group $NR_1R_2$ being selected from the group consisting of pyrrolidino, morpholino, thiomorpholino, piperidino, hexamethyleneimino, piperazino, 4-methylpiperazino, 4-(β-hydroxyethyl)piperazino, 4-phenylpiperazino and 4-(p-chlorophenyl)-piperazino groups; and Ar represents an acetylaminophenyl group of the formula

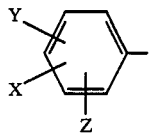

in which X is $CH_3CONH$ and Y and Z, which can be identical or different, each represent a hydrogen or halogen atom; and (b) their addition salts.

The groups $CH_3$, $CH_2CH_3$, $CH_2CH_2CH_3$, $CH(CH_3)_2$, $C(CH_3)_3$, $CH(CH_3)CH_2CH_3$, $CH_2CH(CH_3)_2$ and $CH_2CH_2CH_2CH_3$ may be mentioned in particular among the $C_1$-$C_6$ alkyl groups included in the definitions of the groups $R_1$ and $R_2$.

The cyclopropyl, cyclopentyl and cyclohexyl groups may be mentioned in particular among the $C_3$-$C_6$ cycloalkyl groups included in the definition of the group $R_1$.

The N-heterocyclic groups $NR_1R_2$ suitable according to the invention are advantageously saturated. They comprise from 5 to 7 ring members, can include a second heteroatom selected from the group consisting of N, O and S and can be substituted especially by $C_1$-$C_4$ alkyl groups, $C_1$-$C_4$ hydroxyalkyl groups (especially $CH_2CH_2OH$) or aryl or halogenoaryl groups (especially phenyl and 4-chlorophenyl).

F, Cl and Br may be mentioned as particularly suitable among the halogen atoms included in the definitions of the groups Y and Z, the preferred halogen atom here being Cl. The acetylamino group $X = CH_3CONH$ can be in the ortho, meta or para position, the meta and para positions being preferred. The preferred groups Ar are 4-acetylaminophenyl, 4-acetylamino-3-chlorophenyl, 4-acetylamino-3,5-dichlorophenyl, 3-acetylaminophenyl and 3-acetylamino-4-chlorophenyl groups.

The expression "addition salts" is understood here as meaning firstly the acid addition salts obtained by reacting one of the abovementioned free bases with an inorganic or organic acid, and secondly the ammonium salts, Hydrochloric, hydrobromic, acetic, formic, propionic, oxalic, fumaric, maleic, succinic, benzoic, cinnamic, mandelic, citric, malic, tartaric, aspartic, glutamic, methanesulfonic and p-toluenesulfonic acids may be mentioned in particular among the acids which can be used to salify the abovementioned free bases. $CH_3I$ and $CH_3Cl$ may be mentioned in particular among the compounds making it possible to obtain ammonium salts. In general terms, the acid addition salts are preferred to the ammonium salts.

A number of compounds according to the invention have been collated in Table I below without in any way implying a limitation. The melting points given are instantaneous melting points determined on a Kofler bench.

TABLE I

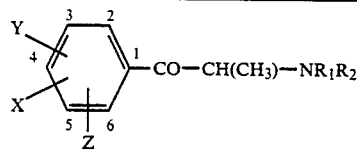

| Product | Code No. | X | Y | Z | NR₁R₂ | Melting point (°C.) |
|---|---|---|---|---|---|---|
| Example 1 (a) | CRL 41 152 | 4-CH₃CONH | H | H | NHCH(CH₃)₂ | 240 |
| Example 2 (a) | CRL 41 177 | 4-CH₃CONH | H | H | NHC(CH₃)₃ | (b) |
| Example 3 (a) | CRL 41 192 | 4-CH₃CONH | 3-Cl | H | NHCH(CH₃)₂ | 260 |
| Example 4 (a) | CRL 41 212 | 4-CH₃CONH | H | H | NH(CH₂)₂CH₃ | 230 (c) |
| Example 5 (a) | CRL 41 217 | 4-CH₃CONH | H | H | NHCH₃ | (d) |
| Example 6 (a) | CRL 41 219 | 4-CH₃CONH | 3-Cl | H | pyrrolidino | 260 |
| Example 7 (a) | CRL 41 220 | 4-CH₃CONH | 3-Cl | 5-Cl | NHCH(CH₃)₂ | (b) |
| Example 8 (a) | CRL 41 224 | 4-CH₃CONH | H | H | NHCH₂CH₃ | 230 (c) |
| Example 9 (a) | CRL 41 232 | 4-CH₃CONH | H | H | N(CH₃)₂ | 252 (c) |
| Example 10 (a) | CRL 41 236 | 4-CH₃CONH | H | H | morpholino | 255 (c) |
| Example 11 (a) | CRL 41 240 | 4-CH₃CONH | H | H | piperidino | 240 (c) |
| Example 12 (e) | CRL 41 242 | 4-CH₃CONH | H | H | N-methylpiperazino | 230 (c) |
| Example 13 (a) | CRL 41 245 | 4-CH₃CONH | H | H | NH-cyclopropyl | 200 (c) |
| Example 14 (a) | CRL 41 247 | 4-CH₃CONH | H | H | thiomorpholino | 200–210 (c) |
| Example 15 (a) | CRL 41 254 | 3-CH₃CONH | H | H | NHCH(CH₃)₂ | 250 (c) |
| Example 16 (a) | CRL 41 259 | 3-CH₃CONH | H | H | N(CH₃)₂ | 250 (c) |
| Example 17 (a) | CRL 41 262 | 3-CH₃CONH | H | H | piperidino | 245 (c) |
| Example 18 (a) | CRL 41 267 | 3-CH₃CONH | H | H | morpholino | 220 (c) |
| Example 19 (a) | CRL 41 269 | 3-CH₃CONH | H | H | thiomorpholino | 250 |
| Example 20 (a) | CRL 41 277 | 3-CH₃CONH | H | H | NH(CH₂)₂CH₃ | 220 (c) |

Notes
(a): hydrochloride;
(b): the melting point is above 260° C.;
(c): with decomposition;
(d): the melting point is above 250° C.;
(e): dihydrochloride.

The new 1-(acetylaminophenyl)-2-aminopropanone derivatives can be prepared in accordance with a method known per se, by the application of classical reaction mechanisms. Two methods of synthesis, represented diagrammatically by the following reactions, are recommended for the preparation of these derivatives:

Variant A:

Variant B:

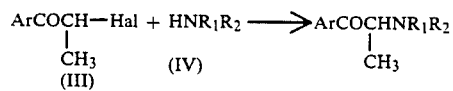

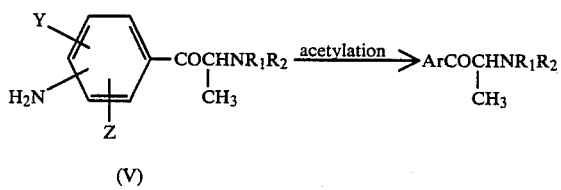

(V)

Variant A consists in reacting a halogen derivative of the formula III (in which Ar is defined as indicated above and Hal represents a halogen atom, in particular Cl or Br and preferably Cl for the yield) with an amine of the formula IV (in which $R_1$ and $R_2$ are defined as indicated above).

Preferably, more than one mol of IV will be used per mol of III, the amine IV participating simultaneously as a reactant and as a solvent or co-solvent for the reaction. The said reaction of the 1-(acetylaminophenyl)-2-halogenopropanone III with the amine IV is advantageously carried out, according to Variant A, for at least 0.5 hour, at a temperature of between 15° C. and the reflux temperature of the reaction medium.

Variant B consists in subjecting a 1-(aminophenyl)-2-aminopropanone derivative of the formula V (in which Y, Z, $R_1$ and $R_2$ are defined as indicated above) to an acetylation reaction by means of an acetylating agent which is in excess relative to the stoichiometric conditions and which is selected from the group consisting of acetyl halides (preferably $CH_3COCl$ for the yield) and acetic anhydride, $(CH_3CO)_2O$. The compounds of the formula V are described in published French patent application FR-A-2 569 184 (filed on Aug. 20, 1984) of the Applicant.

According to Variant B, the derivative of the formula V will advantageously be reacted in $CH_3COCl$, for at least 2 hours, at the reflux temperature of the reaction medium, in a proportion of at least 2 mol of $CH_3COCl$ (preferably 3 to 5 mol of $CH_3COCl$) per mol of V.

In general, it is preferred to use Variant A rather than Variant B for the synthesis of all the 1-(acetylaminophenyl)-2-aminopropanone derivatives. In practice, Variant B is only used for the compounds in which Y=Z=halogen.

The present 1-(acetylaminophenyl)-2-aminopropanone derivatives are useful in therapy. They all act on the CNS, more precisely as antidepressants. They have a stimulant or excitant component in their neuropsychopharmacological profile. In addition to these effects on the CNS, some of these derivatives also have valuable immunological properties; in particular, the products of Examples 7 (CRL 41 220), 12 (CRL 41 242), 14 (CRL 41 247), 15 (CRL 41 254) and 17 (CRL 41 262) have beneficial immunomodulating effects in the treatment of patients having an insufficient immunoreaction, the most valuable products in respect of their immunological properties being the products of Examples 7 (CRL 41 220), 12 (CRL 41 242) and 17 (CRL 41 262).

The best mode for carrying out this invention consists in using, as preferred CNS-active agents, the products of Examples 1 (CRL 41 152, the most preferred compound), 2 (CRL 41 177), 3 (CRL 41 192), 6 (CRL 41 219), 7 (CRL 41 220) and 8 (CRL 41 224).

According to the invention, a therapeutic composition is recommended which contains, in association with a physiologically acceptable excipient, at least one 1-(acetylaminophenyl)-2-aminopropanone derivative or one of its non-toxic addition salts as the active principle.

Of course, in a composition of this type, the active principle is present in a pharmaceutically effective quantity.

Further advantages and characteristics of the invention will be understood more clearly on reading the following description of preparative examples on the one hand and results of pharmacological tests on the other; these data as a whole do not imply a limitation but are given by way of illustration.

PREPARATION I

Preparation of 1-(4-acetylamino-3,5-dichlorophenyl)-2-isopropylaminopropanone hydrochloride

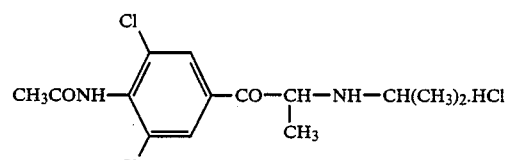

(Example 7; Code No.: CRL 41 220)

28 g of 1-(4-aminophenyl)-2-isopropylaminopropanone are dissolved in 100 ml of distilled water. This solution is stirred for 2 hours and then evaporated to dryness in vacuo. The evaporation residue, which is a brown solid, is taken up in acetic acid and, on recrystallization, gives 11 g (yield: 35%) of 1-(4-amino-3,5-dichlorophenyl)-2-isopropylaminopropanone dihydrochloride.

Melting point (inst.)>260° C.

A mixture of the 11 g of the product thus obtained with 50 ml of $CH_3COCl$ is heated under reflux for 4 hours. The excess acetyl chloride is then evaporated off in vacuo. The evaporation residue is taken up with ethanol to give 9 g (yield: 25%) of CRL 41 220.

Melting point (inst.)>260° C.

PREPARATION II

Preparation of 1-(4-acetylaminophenyl)-2-ethylaminopropanone hydrochloride

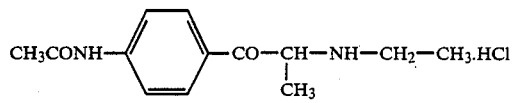

(Example 8; Code No.: CRL 41 224)

a/ 1-(4-Acetylaminophenyl)-2-chloropropanone 92 g (0.72 mol) of 2-chloropropionyl chloride [Cl-CO-CHCl-CH$_3$] are run over a period of 40 minutes into a suspension consisting of 54 g (0.40 mol) of acetanilide, 160 g (1.20 mol) of aluminum chloride and 400 ml of carbon disulfide. The reaction medium is heated under reflux for 1 hour and then poured into a water/ice mixture acidified with dilute hydrochloric acid, and the mixture is then stirred overnight at ambient temperature (15°–25° C.). The precipitate formed is collected by filtration and then purified by recrystallization from benzene to give 78 g (yield: 86.5%) of 1-(4-acetylaminophenyl)-2-chloropropanone.

Melting point (inst.)=120° C.

b/ CRL 41 224

A solution of 25 g (0.11 mol) of 1-(4-acetylaminophenyl)-2-chloropropanone in 164 ml (1.10 mol) of an aqueous solution of ethylamine containing 330 g/liter is heated at about 60°-70° C. for 1 hour. The excess ethylamine is evaporated off under reduced pressure, the evaporation residue is extracted with several portions of ethyl acetate and the dried ethyl acetate phase is then treated with a solution of hydrogen chloride in ethanol. The precipitate formed is purified by washing with hot anhydrous ethanol to give 13.3 g (yield of stage b: 44.7%; overall yield: 38.7%) of CRL 41 224.

Melting point (inst.)=230° C. (with decomposition).

PREPARATION III

Preparation of 1-(4-acetylaminophenyl)-2-piperidinopropanone hydrochloride

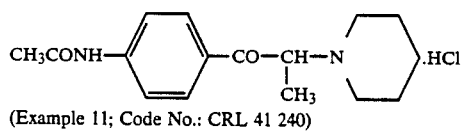

(Example 11; Code No.: CRL 41 240)

A solution consisting of 18 g (0.0798 mol) of 1-(4-acetylaminophenyl)-2-chloropropanone, 78.8 ml (0.7980 mol) of piperidine and 50 ml of water is stirred for 1 hour at normal ambient temperature (15°-25° C.) and then for 0.5 hour under reflux. It is evaporated to dryness under reduced pressure and the evaporation residue is taken up with ethyl acetate. The ethyl acetate phase is washed with water and dried over $Na_2SO_4$ and the solvent is evaporated off to give 25 g of an orange-brown oil. This oil is treated in ethyl acetate with a solution of hydrogen chloride in ethanol.

Purification by crystallization and treatment with carbon black (CXA black) in anhydrous ethanol gives 19.8 g (yield: 79.9%) of CRL 41 240.

Melting point (inst.)=240° C. (with decomposition).

PREPARATION IV

Preparation of 1-(4-acetylaminophenyl)-2-(4-methylpiperazino)propanone dihydrochloride

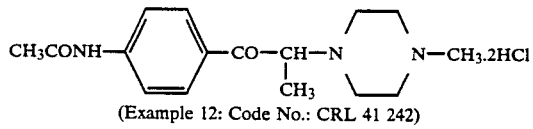

(Example 12: Code No.: CRL 41 242)

A mixture of 18.5 g (0.082 mol) of 1-(4-acetylaminophenyl)-2-chloropropanone and 91 ml (0.820 mol) of 4-methylpiperazine in 60 ml of $H_2O$ is stirred for 1 hour at ambient temperature and then for 0.5 hour under reflux. The reaction medium is taken up with 100 ml of $H_2O$, and 11.6 g of 1-(4-acetylaminophenyl)-2-(4-methylpiperazino)propanone are isolated by filtration.

Melting point (inst.)=90° C.

The free base thus obtained is dissolved in anhydrous ethanol and treated with carbon black (CXA black) and then with a solution of hydrogen chloride in ethanol. The precipitate formed is isolated by filtration to give 14.1 g (yield: 47.5%) of CRL 41 242.

Melting point (inst.)=230° C. (with decomposition).

PREPARATION V

Preparation of 1-(4-acetylamino-3-chlorophenyl)-2-pyrrolidinopropanone hydrochloride

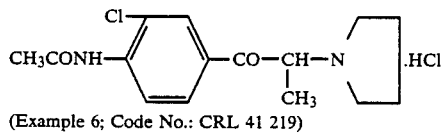

(Example 6; Code No.: CRL 41 219)

a/ 1-(4-Acetylamino-3-chlorophenyl)-2-chloropropanone 45 g (0.199 mol) of 1-(4-acetylaminophenyl)-2-chloropropanone are suspended in 400 ml of $CHCl_3$. 0.2 mol of $Cl_2$ is introduced by bubbling. This gives a yellow solution, which is evaporated to dryness. Recrystallization of the evaporation residue from toluene gives 26 g (yield: 50%) of 1-(4-acetylamino-3-chlorophenyl)-2-chloropropanone.

Melting point (inst.)=118° C.

b/ CRL 41 219

26 g of 1-(4-acetylamino-3-chlorophenyl)-2-chloropropanone are dissolved in a mixture of 100 ml of pyrrolidine and 20 ml of water. The solution is heated under reflux for 2 hours and the excess pyrrolidine is evaporated off in vacuo. The oily evaporation residue is taken up in $C_2H_5OH$ and precipitated by means of HCl gas. This gives 8 g (yield: 24%) of CRL 41 219.

Melting point (inst.)=260° C.

PREPARATION VI

Preparation of 1-(3-acetylaminophenyl)-2-piperidinopropanone hydrochloride

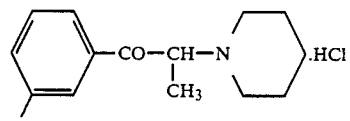

(Example 17; Code No.: CRL 41 262)

a/ 1-(3-Acetylaminophenyl)-2-bromopropanone 30.4 g (0.19 mol) of bromine are run over a period of 2.5 hours, at ambient temperature, into a solution of 37 g (0.19 mol) of 1-(3-acetylaminophenyl)propanone in a mixture of 300 ml of tetrahydrofuran and 300 ml of diethyl ether, in the presence of a trace of $AlCl_3$. The reaction medium is degassed at about 40° C. by means of a stream of nitrogen and evaporated at dryness under reduced pressure. The evaporation residue is purified by crystallization from ethyl acetate to give 26.5 g (yield: 51.6%) of 1-(3-acetylaminophenyl)-2-bromopropanone.

Melting point (inst.)=133° C.

b/ CRL 41 262

A mixture of 18.5 g (0.0685 mol) of 1-(3-acetylaminophenyl)-2-bromopropanone, 68 ml (0.685 mol) of piperidine and 45 ml of water is stirred for 1 hour at ambient temperature. The reaction medium is evaporated to dryness under reduced pressure, the evaporation residue is taken up with ethyl acetate and the insoluble material is removed by filtration. The filtrate is washed with water, dried over Na₂SO₄ and then treated with a solution of hydrogen chloride in ethanol. The precipitate formed is purified by recrystallization from a C₂H₅OH/CH₃OH mixture (3:5 v/v) to give 15 g (yield: 70.7%) of CRL 41 262.

Melting point (inst.)=245° C. (with decomposition).

PREPARATION VII

Preparation of
1-(4-acetylaminophenyl)-2-isopropylaminopropanone hydrochloride

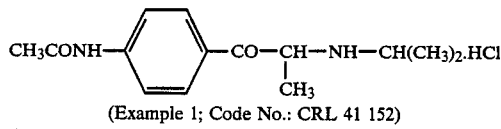

(Example 1; Code No.: CRL 41 152)

(a) 1-(4-Acetylaminophenyl)-2-chloropropanone 27 g of acetanilide are introduced into a mixture comprising 67 g of AlCl₃ and 76.8 g of 2-chloropropionyl chloride [Cl—CO—CHCl—CH₃], at a temperature of between 35° and 45° C. The mixture is stirred until all the acetanilide has dissolved. The reaction medium thus obtained is poured onto crushed ice; the precipitate formed is collected by filtration, washed with water until the pH of the washings is 7, and dried to give 39 g (yield: 86%) of 1-(4-acetylaminophenyl)-2-chloropropanone.

Melting point (inst.)=124° C.

(b) CRL 41 152

The 39 g of 1-(4-acetylaminophenyl)-2-chloropropanone thus obtained are dissolved in 200 ml of isopropylamine. The resulting reaction medium is heated under reflux for 6 hours. The excess isopropylamine is evaporated off in vacuo. The evaporation residue, which is in the form of a viscous oil, is taken up with 200 ml of anhydrous ethanol and the hydrochloride is precipitated by means of a stream of HCl gas. Recrystallization from ethanol gives 40 g (yield: 70%) of CRL 41 152, which is in the form of a very water-soluble white powder.

Melting point=240° C.

PREPARATION VIII

Preparation of
1-(4-acetylamino-3-chlorophenyl)-2-isopropylaminopropanone hydrochloride (Example 3; Code No.: CRL 41 192)

(a)
1-(4-Acetylamino-3-chlorophenyl)-2-chloropropanone 45 g of 1-(4-acetylaminophenyl)-2-chloropropanone are suspended in 400 ml of CHCl₃. 0.2 mol of Cl₂ is introduced by bubbling. The resulting yellow solution is evaporated to dryness. Recrystallization of the evaporation residue from toluene gives 26 g (yield: 50%) of 1-(4-acetylamino-3-chlorophenyl)-2-chloropropanone.

Melting point (inst.)=118° C.

(b) CRL 41 192

The 26 g of 1-(4-acetylamino-3-chlorophenyl)-2-chloropropanone thus obtained are dissolved in 150 ml of isopropylamine. The solution is heated under reflux for 4 hours and the excess isopropylamine is evaporated off in vacuo. The evaporation residue, which is in the form of an oil, is taken up in ethanol and the hydrochloride is precipitated by means of a stream of HCl gas.

This gives 9.6 g (yield: 15%) of CRL 41 192.

Melting point=260° C.

The results of the tests which were undertaken with the compounds according to the invention have been summarized below.

A. TESTS RELATING TO CRL 41 224 (PRODUCT OF EXAMPLE 8)

In the neuropsychopharmacological study which follows, CRL 41 224, in solution in distilled water (pH 6), was administered intraperitoneally in a volume of 20 ml/kg to male mice and 5 ml/kg to male rats.

I. TOXICITY

In male mice, the LD-0 (maximum non-lethal dose) by intraperitoneal administration is greater than 256 mg/kg and less than 512 mg/kg.

II. OVERALL BEHAVIOR AND REACTIVITIES

Groups of three animals are observed before and then 0.25 hour, 0.50 hour, 1 hour, 2 hours, 3 hours and 24 hours after the administration of CRL 41 224. The following observations are made:

1°. in mice at doses of 2 and 8 mg/kg forms of behavior, reactivities and variations in the pupil diameter and rectal temperature all substantially comparable to those of the control group receiving only distilled water;

at a dose of 32 mg/kg excitation for 3 hours, sterotypies lasting between 2 and 3 hours, and an increase in the reactivity to touch and muscular tonus for between 2 and 3 hours;

at a dose of 128 mg/kg excitation for 3 hours, stereotypies lasting between 2 and 3 hours, an increase in the reactivity to touch and muscular tonus for 24 hours, hyperthermia for between 2 and 3 hours (+0.9° C.), and moderate mydriasis for 3 hours;

2°. in rats at a dose of 1 mg/kg brief mydriasis appearing 0.5 hour after administration of CRL 41 224;

at a dose of 4 mg/kg mydriasis lasting 2 hours;

at a dose of 16 mg/kg stereotypies for 3 hours, and mydriasis lasting 3 hours;

at a dose of 64 mg/kg excitation for 1 hour, stereotypies for 3 hours, piloerection for 1 hour, an increase in the reactivity to touch and muscular tonus for 3 hours, hyperthermia for 3 hours (+1.5° C.), and mydriasis for 3 hours.

III. INTERACTION WITH APOMORPHINE 1. in mice

Groups of 6 mice receive CRL 41 224 0.5 hour before the subcutaneous injection of 1 or 16 mg/kg of apomorphine. It is observed that, at doses of 8 mg/kg, 32 mg/kg and 128 mg/kg, CRL 41 224 opposes the hypothermia induced by apomorphine, without modifying the righting behavior and stereotypy behavior.

2. in rats

CRL 41 224 is administered to groups of 6 rats 0.5 hour before the subcutaneous injection of 0.5 mg/kg of apomorphine. It is observed that, at a dose of 16 mg/kg, but especially at a dose of 64 mg/kg, CRL 41 224 causes potentiation of the stereotypies induced by apomorphine.

IV. INTERACTION WITH AMPHETAMINE

Amphetamine (2 mg/kg) is injected intraperitoneally into groups of 6 rats 30 minutes after the administration of CRL 41 224. It is found that, at a dosage of 16 mg/kg, but especially at a dose of 64 mg/kg, CRL 41 224 causes potentiation of the stereotypies induced by amphetamine.

V. INTERACTION WITH RESERPINE

Four hours after the intraperitoneal injection of 2.5 mg/kg of reserpine, groups of 6 mice receive CRL 41 224.

It is noted that, as from a dose of 2 mg/kg, CRL 41 224 opposes the hypothermia induced by reserpine. This antagonism is significant for doses of 32 mg/kg and 128 mg/kg and, at a dose of 128 mg/kg, CRL 41 224 reduces the intensity of the ptosis induced by reserpine.

VI. INTERACTION WITH OXOTREMORINE

CRL 41 224 is administered to groups of 6 mice 0.5 hour before the intraperitoneal injection of 0.5 mg/kg of oxotremorine.

1. Action on the temperature

It is found that, at doses of 2 mg/kg and 8 mg/kg, but especially at doses of 32 mg/kg and 128 mg/kg, CRL 41 224 opposes the hypothermic action of oxotremorine.

2. Action on the trembling

It is found that, at doses of 8 mg/kg and 32 mg/kg, but especially 128 mg/kg, CRL 41 224 distinctly reduces the intensity of the trembling induced by oxotremorine.

3. Action on the peripheral cholinergic symptoms

It is observed that, in practice, CRL 41 224 does not modify the signs of peripheral cholinergic stimulation induced by oxotremorine.

VII. ACTION ON THE FOUR PLATE TEST, TRACTION AND ELECTRIC SHOCK

The test is performed on groups of 10 mice 30 minutes after the administration of CRL 41 224.

It is found that, at a dose of 128 mg/kg, CRL 41 221 causes an increase in the number of punished passes, does not cause major motor incapacity, does not aggravate the convulsant effects and does not modify the lethal effects of electric shock.

VIII. ACTION ON THE SPONTANEOUS MOTILITY 0.5 hour after they have received CRL 41 224, the mice (6 per dose, 12 control animals) are placed in an actimeter, where their motility is recorded for 30 minutes.

It is observed that, at a dose of 8 mg/kg and especially at doses of 32 mg/kg and 128 mg/kg, CRL 41 224 increases the spontaneous motor activity of the mice.

IX. ACTION ON THE INTERGROUP AGGRESSION

After they have stayed for 3 weeks in the 2 halves of a cage divided by an opaque partition, groups of 3 mice receive CRL 41 224. Half an hour later, the two groups from the same cage are brought together by removal of the partition, and the number of fights which occur in 10 minutes is noted. Half the test is performed on ordinary mice (NMRI, C.E.R. January) and half an NMRI (Iffa Credo) mice.

It is found that, at a dose of 128 mg/kg, CRL 41 224 reduces the number of fights.

X. ACTION TOWARDS SOME FORMS OF BEHAVIOR PERTURBED BY VARIOUS AGENTS

1. Motility reduced by habituation to the enclosure

After they have stayed in the actimeters for 18 hours, the mice (6 per dose, 12 control animals) receive CRL 41 224. They are immediately returned to their respective enclosures and, half an hour later, their motility is recorded for 30 minutes.

It is observed that, at doses of 32 mg/kg and 128 mg/kg, CRL 41 224 causes a distinct resumption in the motor activity of mice accustomed to their enclosure.

2. Motility reduced by hypoxic aggression

Half an hour after they have received CRL 41 224, the mice (10 per dose, 20 control animals) are subjected to acute hypobaric anoxia [pressure reduction of 600 mm Hg (i.e. about $8 \times 10^4$ Pa) in 90 seconds; release of vacuum in 45 seconds] and are then placed in an actimeter, where their motility is recorded for 10 minutes.

It is observed that, at doses of 8 mg/kg, 32 mg/kg and especially 128 mg/kg, CRL 41 224 causes a distinct improvement in the motor recovery in mice whose motility has been depressed following a brief period in a reduced-pressure enclosure.

3. Asphyxiant anoxia

Groups of 10 mice receive CRL 41 224 half an hour before the intraperitoneal administration of 32 mg/kg of gallamine triiodoethylate (reference curarizing agent).

It is observed that CRL 41 224 does not change the time taken for convulsions and death to occur following asphyxiant anoxia caused by a curarizing agent.

XI. INTERACTION WITH BARBITAL

Half an hour after the administration of CRL 41 224, groups of 10 mice receive an intraperitoneal injection of barbital (220 mg/kg).

It is found that, as from a dose of 2 mg/kg, CRL 41 224 reduces the duration of the sleep induced by barbital (total antagonism is obtained at 32 mg/kg).

XII. ACTION ON THE "BEHAVIORAL DESPAIR"

Half an hour after they have received CRL 41 224, groups of 6 mice are placed in a beaker filled with water to a height of 6 cm. The total period of immobility between the 2nd and 6th minutes following immersion is noted.

It is observed that, at doses of 8 mg/kg and especially 32 mg/kg and 128 mg/kg, CRL 41 224 reduces the period of immobility of mice which have been forcibly immersed.

XIII. CONCLUSIONS

The above neuropsychopharmacological tests as a whole show that CRL 41 224 has antidepressant effects: antagonism of the hypothermia induced by apomorphine, reserpine or oxotremorine, and reduction in the period of immobility or of "despair";

stimulant effects: excitation in mice, presence of stereotype movements in mice and rats, potentiation of the stereotypies induced by apomorphine and amphetamine, increase in the motor activity, improvement in the motor recovery in mice whose motility has been depressed following a brief period in a reduced-pressure enclosure, and distinct resumption in the motor activity of mice accustomed to their enclosure; and peripheral α-adrenergic stimulant effects: mydriasis and antagonism of the ptosis induced by reserpine, and piloerection.

It follows that CRL 41 224 behaves as an antidepressant for the CNS. The antidepressant effect is associated, at the same doses, with a distinct stimulant component.

B. TESTS RELATING TO CRL 41 219 (PRODUCT OF EXAMPLE 6)

The neuropsychopharmacological study of CRL 41 219 was carried out as indicated above for CRL 41 224. The results have been given below.

By intraperitoneal administration to male mice, the LD-30 (lethal dose for 30% of the animals tested) is of the order of 128 mg/kg and the LD-50 is of the order of about 200 mg/kg.

Briefly, CRL 41 219 has a profile characterized by stimulant effects:

in mice:

excitation with hyperreactivity, hyperactivity, increase in the spontaneous motor activity, resumption in the motor activity after habituation to the enclosure, improvement in the motor recovery after hypoxic aggression, and increase in the number of punished passes in the 4 plate test, late appearance of stereotypies, antagonism of the sleep induced by barbital;

in rats:

excitation (with hyperreactivity), presence of stereotype movements and potentiation of the stereotypies induced by apomorphine and amphetamine;

antidepressant effects:

antagonism of the hypothermia induced by apomorphine, reserpine and oxotremorine, reduction in the immobility of so-called "despair";

effects reflecting peripheral α-adrenergic stimulation:

antagonism of the ptosis induced by reserpine, mydriasis, antagonism of the trembling caused by oxotremorine.

Furthermore, CRL 41 219 seems to favor or potentiate the effects of convulsant agents (aggravation of the lethal effects of electric shock, reduction in the time taken for convulsions and death to occur following asphyxiant anoxia).

These results as a whole show that CRL 41 219 is a substance possessing antidepressant, stimulant and arousing properties.

C. TESTS RELATING TO CRL 41 220 (PRODUCT OF EXAMPLE 7)

The neuropsychopharmacological study of CRL 41 220 was carried out in accordance with the procedures given above for CRL 41 224.

I. TOXICITY

By intraperitoneal administration to male mice, CRL 41 220 has the following LD-0, LD-30 and LD-50:

LD-0: greater than 128 mg/kg,
LD-30: of the order of about 250 mg/kg,
LD-50: of the order of about 500 mg/kg.

II. ACTION ON THE CNS

CRL 41 220 has antidepressant and stimulant effects.

III. CARDIOVASCULAR ACTION

Four dogs (average weight: 13.8 kg), anesthetized with nembutal, receive CRL 41 220 by intraduodenal administration at successive doses of 0.1 mg/kg, 0.5 mg/kg, 1 mg/kg, 2.5 mg/kg, 5 mg/kg and 10 mg/kg. The blood pressure, the heart beat, the flow rate through the femoral artery, the flow rate through the vertebral artery and the rectal and/or skin temperature are measured and the coloration of the skin and the bile (collected by catheterization of the bile duct after ligature of the cystic duct) is observed.

It is found that, when administered intraduodenally, CRL 41 220 increases the vertebral flow rate as from a dose of 0.5 mg/kg, the femoral flow rate at a dose of 1 mg/kg and the heart beat at a dose of 2.5 mg/kg, has a hypotensive effect at a dose of 10 mg/kg, induces respiratory stimulation in the 4 dogs, and increases the rectal and skin temperatures.

The effects of isoprenaline, tested after the intraduodenal administration of CRL 41 220 at an accumulated dose of 19.1 mg/kg, are not modified as regards the heart beat and are very slightly modified as regards the diastolic blood pressure: with 10 μg/kg of isoprenaline, the diastolic blood pressure changes from 112 mm Hg (i.e. about $1.49 \times 10^4$ Pa) to 47 mm Hg (i.e. about $6.26 \times 10^3$ Pa) instead of 158 mm Hg (i.e. about $2.1 \times 10^4$ Pa) in the control animals, and the heart beat changes from 221 beats/minute to 275 beats/minute instead of from 175 beats/minute to 280 beats/minute in the control animals (the dogs used for the tests also being used as the control animals).

The hypertension induced by noradrenaline is reduced: with 2 μg/kg of noradrenaline, the systolic blood pressure changes from 202 mm Hg (i.e. about $2.69 \times 10^4$ Pa) to 272 mm Hg (i.e. about $3.62 \times 10^4$ Pa) after the intraduodenal administration of CRL 41 220, instead of from 199 mm Hg (i.e. about $2.65 \times 10^4$ Pa) to 323 mm Hg (i.e. about $4.3 \times 10^4$ Pa) in the control animals.

Briefly, CRL 41 220 acts as a hypotensive agent (the hypotensive effects resulting from the reduction in the diastolic blood pressure). As the injection of 1 mg/kg of propanolol at the end of the test suppresses all the effects of CRL 41 220, it is assumed that this product acts on the cardiovascular system by stimulating the β-adrenergic receptors.

IV. IMMUNOLOGICAL PROPERTIES

The test for cells forming lysis areas according to the technique of A. J. CUMMINGHAM et al. ("Further improvements in the plaque technique for detecting single antibody forming cells"), Immunology 14, pages 599–601 (1968), and measurement of the intensity of the delayed hypersensitivity to the red blood corpuscles of sheep according to the technique of T. E. MILLER et al. ("Immunopotentiation with BCG II modulation of the response to sheep blood cells"), Journal of the National Cancer Institute 51, (No. 5), pages 1669–1676 (1973), have made it possible to demonstrate the immunomodulating stimulant capacity of CRL 41 220.

V. COMPLEMENTARY TESTS

CRL 41 220 was shown to be active in the study of LEWIS' carcinoma in mice, according to the following protocol:

a. animals: consanguineous female mice ($C_{57}BL_6$), b. infecting cells: $10^5$ cells injected subcutaneously into the back of the animals, c. monitoring of the tumor growth by measurement of the tumor twice a week, d. evaluation of the pulmonary metastases after fixation of the lungs of the dead animals in BOUIN's fixative.

Under these operating conditions, CRL 41 220 used by itself appears to be inactive, whereas, on the one hand, cyclophosphamide (reference anticancer agent), at a dose of 100 mg/kg, reduces the number of plumonary metastases and slightly slows down the development of tumors without however improving the survival of the animals treated, and on the other hand, at a dose of 150 mg/kg, it distinctly opposes the process initiated by the administration of infecting cells (survival of 2 out of 6 animals).

Using the same procedures, the association of CRL 41 220 with 150 mg/kg of cyclophosphamide gives the results collated in Table II below.

TABLE II

| association | | |
|---|---|---|
| cyclophosphamide | CRL 41 220 | results |
| 150 mg/kg | 100 mg/kg | increase in the toxicity compared with cyclophosphamide used by itself |
| 150 mg/kg | 5 mg/kg | substantially few differences compared with cyclophosphamide used by itself |
| 150 mg/kg | 2 mg/kg | unquestionable protective action in respect of LEWIS' carcinoma, all the animals treated still being alive several weeks after the experiment |

VI. CLINICAL TRIALS

CRL 41 220, administered orally to man at a dose of 250 to 500 mg (per gelatine capsule or tablet) gave good results in the treatment of patients presenting with circulatory disorders and having an insufficient immunoreaction, for example in cases of recurrent herpes, rheumatoid polyarthritis and severe forms of measles.

D. TESTS RELATING TO CRL 41 232 (PRODUCT OF EXAMPLE 9)

The neuropsychopharmacological study of CRL 41 232 was carried out according to the procedures given above for CRL 41 224.

I. TOXICITY

When administered intraperitoneally to male mice, CRL 41 232 has an LD-0 greater than 128 mg/kg and an LD-30 of the order of about 250 mg/kg.

II. ACTION ON THE CNS

Briefly, CRL 41 232 has antidepressant effects: antagonism of the hypothermia induced by apomorphine, reserpine and oxotremorine, and reduction in the period of immobility or "despair";

stimulant effects: excitation in mice, presence of stereotype movements in mice and rats, potentiation of the stereotypies induced by apomorphine and amphetamine, increase in the motor activity, improvement in the motor recovery in mice whose motility has been depressed following a brief period in a reduced-pressure enclosure, and distinct resumption in the motor activity of mice accustomed to their enclosure; and peripheral α-adrenergic stimulation: mydriasis, exophthalmos and antagonism of the ptosis induced by reserpine.

CRL 41 232 behaves overall as a stimulant and antidepressant for the CNS.

E. TESTS RELATING TO CRL 41 236 (PRODUCT OF EXAMPLE 10)

The neuropsychopharmacological study of CRL 41 236 was carried out according to the procedures given above for CRL 41 224.

I. TOXICITY

When administered intraperitoneally to male mice, CRL 41 236 has an LD-0 greater than 256 mg/kg and an LD-30 of the order of about 500 mg/kg.

II. ACTION ON THE CNS

Briefly, CRL 41 236 possesses antidepressant effects: antagonism of the hypothermia induced by apomorphine, reserpine and oxotremorine, and reduction in the immobility or "despair";

stimulant effects: excitation with hyperreactivity, without the presence of stereotype movements, hyperactivity (increase in the spontaneous motility and in the motor activity after habituation to the enclosure), improvement in the motor recovery after hypoxic aggression, moderate increase in the number of punished passes in the 4 plate test, potentiation of the stereotypies induced by apomorphine and amphetamine, and antagonism of the sleep induced by barbital;

peripheral α-adrenergic stimulation: antagonism of the ptosis induced by reserpine, and mydriasis.

Furthermore, CRL 41 236 seems to aggravate the lethal effects of electric shock.

Consequently, CRL 41 236 behaves as an antidepressant having stimulant and arousing properties.

F. TESTS RELATING TO CRL 41 240 (PRODUCT OF EXAMPLE 11)

Following the procedures described above for the study of CRL 41 224, the following properties were observed.

I. TOXICITY

When administered intraperitoneally to male mice, CRL 41 240 has an LD-0 greater than 250 mg/kg.

II. ACTION ON THE CNS

Briefly, CRL 41 240 possesses antidepressant effects: antagonism of the hypothermia induced by apomorphine, reserpine and oxotremorine, and reduction in the period of immobility or "despair" (this reduction perhaps being related to the stimulant component);

stimulant and arousing effects: excitation in mice and rats with the presence of stereotype movements and potentiation of the stereotypies induced by apomorphine and amphetamine, increase in the motor activity, improvement in the motor recovery in mice whose motility has been depressed following a brief period in a reduced-pressure enclosure, resumption in the activity of mice accustomed to their enclosure, and very distinct antagonism of the sleep induced by barbital;

peripheral α-adrenergic stimulation: mydriasis, exophthalmos and antagonism of the ptosis induced by reserpine; and anticonvulsant effects at a high dose: antagonism of the convulsant effects of electric shock and increase in the time taken for asphyxiant convulsions to occur.

It follows that CRL 41 240 behaves as an antidepressant and stimulant for the CNS.

G. TESTS RELATING TO CRL 41 242 (PRODUCT OF EXAMPLE 12)

The neuropsychopharmacological study of CRL 41 242 was carried out according to the procedures described above for CRL 41 224, except that the pH of the aqueous solution of CRL 41 242 to be injected intraperitoneally varies as a function of the concentration in the manner indicated in Table III below.

TABLE III pH OF THE AQUEOUS SOLUTION TO BE INJECTED, AS A FUNCTION OF THE CONCENTRATION OF CRL 41 242.

| Concentration of CRL 41 242 | pH |
| --- | --- |
| 50 g/liter | 2.5 |
| 13 g/liter | 3.0 |
| 2 g/liter | 3.5 |
| 0.8 g/liter | 4.0 |
| 0.4 g/liter | 4.5 |
| 0.2 g/liter | 5.0 |
| ≦0.05 g/liter | 5.5 |

I. TOXICITY

When administered intraperitoneally to male mice, CRL 42 242 has an LD-0 greater than 256 mg/kg and an LD-60 of the order of about 500 mg/kg.

II. ACTION ON THE CNS

Briefly, CRL 41 242, at high doses, has sedative effects manifested by:

sedation in mice and rats with a decrease in the reactivities and hypothermia in mice, a decrease in the spontaneous motility and the number of punished passes in the four plate test on mice, a reduction in the intergroup aggression in mice, an increase in the duration of the sleep induced by barbital in mice, an increase in the time taken for convulsions and death to occur following asphyxiant anoxia; and antidepressant effects manifested by:

very moderate antagonism of the hypothermia induced by oxotremorine, and a slight reduction in the period of immobility of mice which have been forcibly immersed.

CRL 41 242 also has very discreet effects of the stimulant type at weak doses.

III. IMMUNOLOGICAL PROPERTIES

CRL 41 242 was shown to be particularly valuable as an immunostimulant substance.

H. TESTS RELATING TO CRL 41 245 (PRODUCT OF EXAMPLE 13)

The neuropsychopharmacological study of CRL 41 245 was carried out according to the procedures described above for CRL 41 224.

I. TOXICITY

When administered intraperitoneally to male mice, CRL 41 245 has an LD-0 greater than 256 mg/kg and an LD-100 less than or equal to about 512 mg/kg.

II. ACTION ON THE CNS

Briefly, under experimental conditions, CRL 41 245 has antidepressant effects:

antagonism of the hypothermia induced by apomorphine, reserpine and oxotremorine, reduction in the period of immobility of mice which have been forcibly immersed (perhaps associated with a stimulant component);

stimulant and arousing effects:

excitation with hyperreactivity in mice and rats, increase in the spontaneous motor activity of mice with resumption in the motor activity of mice accustomed to their enclosure, and improvement in the motor recovery in mice subjected to acute hypoxia, increase in the number of punished passes in the 4 plate test on mice, reduction in the duration of the sleep induced by barbital, presence of stereotype movements in mice and rats and potentiation of the stereotypies induced by apomorphine and amphetamine in rats; and peripheral α-adrenergic stimulation:

piloerection in mice and rats, mydriasis in rats, reduction in the ptosis induced by reserpine in mice.

Furthermore, CRL 41 245 shows total antagonism, at a strong dose, of the convulsant effects of electric shock, a reduction, at a strong dose, in the intensity of the trembling due to oxotremorine, and a reduction in the intergroup aggression.

In conclusion, CRL 41 245 behaves as an antidepressant with a strong stimulant component.

I. TESTS RELATING TO CRL 41 254 (PRODUCT OF EXAMPLE 15)

The neuropsychopharmacological study of CRL 41 254 was carried out according to the procedures described above for CRL 41 224.

I. TOXICITY

When administered intraperitoneally to male mice, CRL 41 254 has an LD-0 greater than 256 mg/kg and an LD-100 less than or equal to 512 mg/kg.

II. ACTION ON THE CNS

At strong doses, CRL 41 254 has modest antidepressant effects (antagonism of the hypothermia induced by apomorphine and oxotremorine—but no antagonism of the hypothermia induced by reserpine) and weak stimulant effects (firstly a reduction in the duration of the sleep induced by barbital, and secondly a moderate resumption in the motor activity of mice accustomed to their enclosure).

III. IMMUNOLOGICAL PROPERTIES

At a dose of 1 mg/kg, CRL 41 254 has a statistically significant immunostimulant activity according to the test for cells forming lysis areas after immunization by means of red blood corpuscles of sheet ("PFCIgM" test), described by A. J. CUNNINGHAM et al., Immunology 14, pages 599–601 (1968), as mentioned above, and at doses of 10 to 100 mg/kg administered orally, it has a statistically significant immunostimulant activity according to the measurement of the intensity of the delayed hypersensitivity to red blood corpuscles of sheep, described by T. E. MILLER et al., Journal of the National Cancer Institute, 51 (No. 5), pages 1669–1676 (1973), as mentioned above.

J. TESTS RELATING TO CRL 41 262 (PRODUCT OF EXAMPLE 17)

CRL 41 262 has antidepressant and stimulant effects on the CNS. It was shown to be particularly valuable as an immunomodulator because of its immunostimulant activity at doses of 0.1 mg/kg, 10 mg/kg and 100 mg/kg according to the abovementioned PFCIgM test, and at doses of 10 and 100 mg/kg, administered orally, according to the abovementioned measurement of the intensity of the delayed hypersensitivity to red blood corpuscles of sheep.

K. TESTS RELATING TO CRL 41 247 (PRODUCT OF EXAMPLE 14)

The neuropsychopharmacological study of CRL 41 247 was carried out according to the procedures described above for CRL 41 224, the CRL 41 247 to be tested being in solution in distilled water at pH 4.5–5.5.

I. TOXICITY

When administered intraperitoneally to male mice, CRL 41 247 has an LD-0 greater than 512 mg/kg and an LD-60 of the order of about 1000 mg/kg.

II. ACTION ON THE CNS

Briefly, at strong doses only, CRL 41 247 has discreet *antidepressant effects* manifested by very moderate antagonism of the hypothermia induced by apomorphine and oxotremorine (but no antagonism towards the hypothermia induced by reserpine) and by a reduction in the period of immobility of mice which have been forcibly immersed; and *stimulant effects* manifested by an increase in the motor activity of mice after habituation to their enclosure and after acute hypoxia.

It is also observed that, at strong doses, CRL 41 247 produces hypothermia (of −3.3° C., 30 minutes after the intraperitoneal administration of 256 mg/kg of CRL 41 247), a reduction in the convulsant effects of electric shock and potentiation of the stereotypies induced by amphetamine.

III. IMMUNOLOGICAL PROPERTIES

It is observed that CRL 41 247 stimulates cell activity according to the abovementioned technique of T. E. MILLER et al.

L. TESTS RELATING TO THE PRODUCTS OF EXAMPLES 1–5

When administered intraperitoneally, CRL 41 152 (Example 1), CRL 41 177 (Example 2), CRL 41 192 (Example 3), CRL 41 212 (Example 4) and CRL 41 217 (Example 5), according to the invention, all have (i) stimulant effects which appear especially as
  excitation with hyperreactivity in mice,
  an increase in the spontaneous motility in mice,
  a resumption in the motor activity of mice accustomed to their enclosure,
  an improvement in the motor recovery in mice after acute hypoxia,
  stereotype movements in rats,
  antagonism of the sleep induced by barbital, and
  potentiation of the stereotypies induced by apomorphine or amphetamine; (ii) antidepressant effects which appear especially as:
  antagonism of the hypothermia induced by apomorphine, oxotremorine or reserpine, and
  a reduction in the immobility or so-called "despair";
  (iii) effects which may reflect peripheral adrenergic stimulation (especially mydriasis, antagonism of the ptosis induced by reserpine and antagonism of the trembling caused by oxotremorine), whereas other signs of α-adrenergic stimulation, such as salivation and exophthalmos, are absent.

CRL 41 152, CRL 41 177, CRL 41 192, CRL 41 212 and CRL 41 217 all differ from the amphetamines by the fact that the stereotype movements which they induce in rats are not suppressed by the prior injection of alpha-methyl-tyrosine (which is a reference substance blocking the catecholamine synthesis, this circumstance preventing the appearance of the stereotypies induced by amphetamine).

Furthermore, it is noted that, in contrast to CRL 41 192 and amphetamines, CRL 41 152, CRL 41 177, CRL 41 212 and CRL 41 217 do not increase the toxicity to grouped mice compared with isolated mice.

Finally, CRL 41 152, CRL 41 192 and CRL 41 212 have anticonvulsant effects towards the convulsions caused especially by electric shock, whereas CRL 41 177 and CRL 41 217 potentiate the convulsant effects of electric shock.

Moreover, when CRL 41 177 is administered gastrically to male mice (in solution in distilled water in a volume of 20 ml/kg), it is found that (i) its effect on spontaneous motilith and (ii) its interaction with barbital are greater than on intraperitoneal administration.

M. SUPPLEMENTAL TESTS RELATING TO CRL 41 152 (PRODUCT OF EXAMPLE 1)

Further tests were carried out in order to point out the mechanism of action of CRL 41 152 in the organism. In these tests that product in solution in distilled water was administered in a volume of 20 ml/kg to male mice and of 5 ml/kg to male rats per I.P. route.

a. Action on stereotypies in rats

Since (i) 41 152 administered per I.P. route to rats induces stereotype movements, and (ii) α-methyltyrosine, a substance of reference which is known to inhibit the synthesis of catecholamines in situ and to prevent almost totally the appearance of the stereotypies induced by amphetamine and amphetamine-like compounds, causes a slight inhibition of the sterotypies induced by CRL 41 152 (128 mg/kg of α-methyltyrosine administered per I.P. route 2.5 hours before administration per I.P. route of 30 mg/kg of CRL 41 152, cause an inhibition of 4% of the CRL 41 152 induced stereotypies), further assays were performed against haloperidol, reserpine and reserpine together with α-methyltyrosine.

Interaction with haloperidol

Batches of rats were administered per I.P. route with haloperidol 0,5 hour before the I.P. injection of CRL 41 152 or amphetamine. Haloperidol at the dose of 0.25 mg/kg, almost totally prevents the appearance of stereotypies induced by CRL 41 152 and amphetamine, and, at the dose of 0.5 mg/kg totally inhibits the said stereotypies.

Interaction with reserpine

Batches of 6 male rats each were administered per I.P. route with 4 mg/kg of reserpine either 4 hours or 24 hours before administration of CRL 41 152 or methylphenidate. Reserpine administered 4 hours before CRL 41 152 or methylphenidate totally prevents the appearance of the stereotype movements induced by CRL 41 152 and methylphenidate. Reserpine administered 24 hours before CRL 41 152 or methylphenidate causes only a moderate reduction of the stereotypies induced by CRL 41 152 and methylphenidate.

Interaction with reserpine and α-methyltyrosine

Batches of 6 rats each were administered with 4 mg/kg I.P. of reserpine (at $T-24$ h), with 128 mg/kg I.P. of α-methyltyrosine (at $T-2,5$ h) then with CRL 41 152 or methylphenidate (at $T=0$). They were immediately placed into transparent enclosures for counting the stereotype movements that are normally induced by said CRL 41 152 and methylphenidate. It was observed that such an association of reserpine and α-methyltyrosine almost totally prevents the appearance of the stereotype movements provoked by CRL 41 152 and methylphenidate.

Comments

According to the results of these assays it seems that:
(i) in view of the results of the interaction with haloperidol test, the CRL 41 152-induced stereotype movements would surely involve the stimulation of a post-synaptic dopaminergic receptor,
(ii) in view of the results of the tests of interaction with reserpine and with the reserpine/α-methyltyrosine association, CRL 41 152 would not exhibit a direct action on the post-synaptic dopaminergic receptor,
(iii) consequently, CRL 41 152 would undirectly act on the post-synaptic dopaminergic system. To be precise CRL 41 152 should involve
1. The liberation of newly synthetized dopamine (as illustrated by the non-complete inhibition by α-methyltyrosine of stereotype movements induced by CRL 41 152), and
2. The participation of the dopamine issued from a pool comprising the newly synthetized catecholamines, as the result of the inhibition of the dopamine recapture mechanism.

b. Influence of catecholamines on hyperactivity

A further series of assays was carried out on mice according to the teaching of S. L. HANDLEY et al. "Influences of catecholamines on dexamphetamine, induced changes in locomotor activity", Psychopharmacology 58, 283–288 (1978), in order to observe a potential influence of dopamine or moradrenaline on the hyperactivity induced by CRL 41 152.

After a habituation period of 1.5 h to the actimeters, male mice (grouped into batches of 10 animals each and a control batch of 20 animals) were administered (under slight anesthesia with ether) per intraventriculocerebral injection (i.e. I.V.C. route) with (i) either 10 μg of noradrenaline, or 10 μg of dopamine or 10 μl (0.5 μl/second) of saline solution, then (ii) 5 minutes later, with CRL 41 152 (in solution in distilled water) per I.P. route in a volume of 20 ml/kg, immediately before replacing the mice in the actimeters wherein their motility was recorded for 1 hour by measuring the number of crossed rays per period of 5 minutes). Batches receiving CRL 41 152 per I.P. route with noradrenaline or dopamine per I.V.C. route were compared with (i) the control batch receiving the saline solution per I.V.C. route then distilled water per I.P. route, and (ii) batches receiving only noradrenaline, dopamine (per I.V.C. route) or CRL 41 152 (per I.P. route). At the dose of 8 mg/kg, CRL 41 152 induced a distinct statistically significant increase in motor activity which appeared after injection and continued during the one-hour recording.

The I.V.C. administration of 10 μg of noradrealine a 10 μg of dopamine did not cause any visible locomotor effect by comparison with the I.V.C. administration of the saline solution.

The prior I.V.C. administration of noradrenaline induced a distinct statistically significant decrease in the motor stimulant effect caused by CRL 41 152.

Unlike noradrenaline, the prior I.V.C. administration of dopamine did not modify the motor caused by CRL 41 152.

These results clearly show that CRL 41 152 is differing from reference compounds known as stimulant agents (such as amphetamine, methylphenidate, nomifensine, cocaine) the motor effects of which are potentialized by I.V.C. administration of noradrenaline.

The favourable decrease in CRL 41 152 hypermotibility caused by the I.V.C. administration of noradrenaline cannot be explained by the Applicant in the light of his present knowlegde.

(c) Interaction with proadifen

Proadifen is a reference compound (coded as SKF 525-A) which inhibits hepatic microsomial enzymes and accordingly induces hypomotility in mice, and does not oppose the hypothermic effect of apomorpholine.

Two series of experiments were carried out. In the first one, male mice (12 per dose, 12 control animals) were administered per I.P. route (i) with proadifen (75 mg/kg) at T−3 h, then (ii) with CRL 41 152 at T−0,5 h. At T=0 the mice were placed in actimeters, where their motility was recoded for 0.5 h. In the second one male mice (12 per dose, 12 control animals) were administered with proadifen and CRL 41 152 as indicated hereinabove, then subcutaneously with apomorphine (16 mg/kg) at T=0 in order to appreciate the potential variation of the hypothermia induced by apomorphine.

In these two series CRL 41 152, in solution in distilled water, was administered per I.P. route to male mice in a volume of 20 ml/kg.

motility

CRL 41 152 administered alone increases the spontaneous motility in mice. This effect increases with the doses.

Proadifen administered alone induced hypomotility.

The administration of proadifen then CRL 41 152 does not cause a distinct reduction of the hypermotility which is induced by CRL 41 152.

This mainly suggests that the CRL 41 152 hypermotility does not arise from its transformation into an active metabolite (the alternate possibility that there is a transformation of said CRL 41 152, which follows an enzymatic metabolite route that is not affected by proadifen, should be discarded according to the opinion of the Applicant).

Temperature variations

CRL 41 152 exhibits at a dose of 8 mg/kg and especially at a dose of 32 mg/kg an antagonism vis-á-vis the hypothermia induced by apomorphine.

Proadifen exhibits, when used alone, an important hypothermic effect, but it does not modify the hypothermia by apomorphine.

In the other hand proadifen does block the antagonism exhibited by CRL 41 152 vis-á-vis the hypothermic effect of apomorphine.

Neither proadifen, nor CRL 41 152, nor their combination modify the righting behaviour (i.e. =verticalization") and stereotypies induced by apomorphine.

This suggests that the antagonism of the CRL 41 152, which is exhibited against the apomorpholine-induced hypothermia, seems to arise from the transformation of said CRL 41 152 into an active metabolite.

In short, with respect to hypermotility, CRL 41 152 seems mainly to act by itself, while with respect to apomorholine-induced hypothermia said CRL 41 152 seems to act through a metabolite compound.

d. Interaction with barbital

The cinetic study of the interactions with barbital (administration per gastric route), clearly showed the interest of CRL 41 152 as awakening agent in the treatment of hypersomnia and GELINEAU's disease.

(e) Teratogenic study

Assays carried out on White New Zealand gravid female rabbits showed that CRL 41 152 does not exhibit any harmful teratogenic effect and can be administered accordingly to expectant women without trouble during pregnancy.

In clinical trials, CRL 41 152 was shown to be an excellent drug for treating depressions in man as well as hypersomnia and GELINEAU's disease, in the form of tablets or gelatine capsules each containing from 5 mg to 75 mg of active principle, at a rate of 1 to 3 individual doses per day, and CRL 41 177 was also shown to be an excellent antidepressant drug in the form of tablets or gelatine capsules each containing 2 mg of active principle, at a rate of 2 to 3 tablets or gelatine capsules per day.

What is claimed is:

1. A compound of the formula:

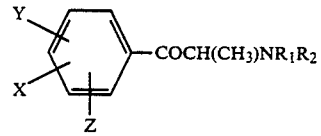

wherein $NR_1R_2$ is pyrrolidino, morpholino, thiomorpholino, hexamethyleneimino, piperazino, 4-methylpiperazino, 4-($\beta$-hydroxyethyl)piperazino, 4-phenylpiperazino or 4-(p-chlorophenyl) piperazino, X is $CH_3CONH$, and Y and Z are independently hydrogen or halogen; or an addition salt thereof.

2. The compound according to claim 1, wherein

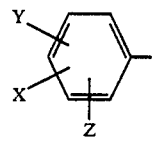

is 4-acetylaminophenyl, 4-acetylamino-3-chlorophenyl, 4-acetylamino-3,5-dichlorophenyl, 3-acetylaminophenyl or 3-acetylamino-4-chlorophenyl.

3. The compound according to claim 1 that is 1-(4-acetylaminophenyl)-2-morpholinopropanone or a non-toxic addition salt thereof.

4. The compound according to claim 1 that is 1-(3-acetylaminophenyl)-2-morpholinopropanone or a non-toxic addition salt thereof.

5. The compound according to claim 1 that is 1-(4-acetylaminophenyl)-2-(4-methylpiperazino)propanone or a non-toxic addition salt thereof.

6. The compound according to claim 1 that is 1-(4-acetylamino-3-chlorophenyl)-2-pyrrolidinopropanone or a non-toxic addition salt thereof.

7. The compound according to claim 1 that is 1-(3-acetylaminophenyl)-2-thiomorpholinopropanone or a non-toxic addition salt thereof.

8. The compound according to claim 1 that is 1-(4-acetylaminophenyl)-2-thiomorpholinopropanone or a non-toxic addition salt thereof.

9. A central nervous system antidepressant composition comprising an effective amount of at least one compound according to claim 1, or a non-toxic addition salt thereof, and a physiologically acceptable excipient.

* * * * *